United States Patent [19]

Audeh et al.

[11] 4,265,735

[45] May 5, 1981

[54] ZSM-5 ZEOLITE CATALYZES DIALKYL DISULFIDE CONVERSION TO HYDROGEN SULFIDE

[75] Inventors: Costandi A. Audeh; Clarence D. Chang, both of Princeton; William H. Lang, Pennington, all of N.J.

[73] Assignee: Mobil Oil Corporation, Fairfax, Va.

[21] Appl. No.: 106,320

[22] Filed: Dec. 21, 1979

[51] Int. Cl.$^3$ ............................................. C07C 19/00
[52] U.S. Cl. .................................. 208/234; 585/408; 585/733; 208/235
[58] Field of Search ................ 208/234, 235; 585/408, 585/733

[56] References Cited

U.S. PATENT DOCUMENTS

| 2,285,696 | 6/1942 | Dunn | 585/733 |
| 2,740,749 | 4/1956 | Meguerian et al. | 208/234 |
| 3,728,408 | 4/1973 | Tobias | 585/408 |
| 3,821,103 | 6/1974 | Owell et al. | 208/72 |
| 3,894,106 | 7/1975 | Chang | 585/408 |
| 3,894,107 | 7/1975 | Butter et al. | 585/408 |

OTHER PUBLICATIONS

C. D. Chang et al. J. Catalysis, 47, 247-249 1977.

Primary Examiner—Veronica O'Keefe
Attorney, Agent, or Firm—C. A. Huggett; V. J. Frilette

[57] ABSTRACT

Dialkyl disulfide waste, such as that formed in a caustic wash process for removing mercaptans from a hydrocarbon stream, is converted to hydrogen sulfide and valuable hydrocarbons by catalytic contact with a highly siliceous zeolite catalyst exemplified by ZSM-5. The hydrogen sulfide in turn is readily converted to marketable sulfur, thus alleviating the waste disposal problem.

11 Claims, 1 Drawing Figure

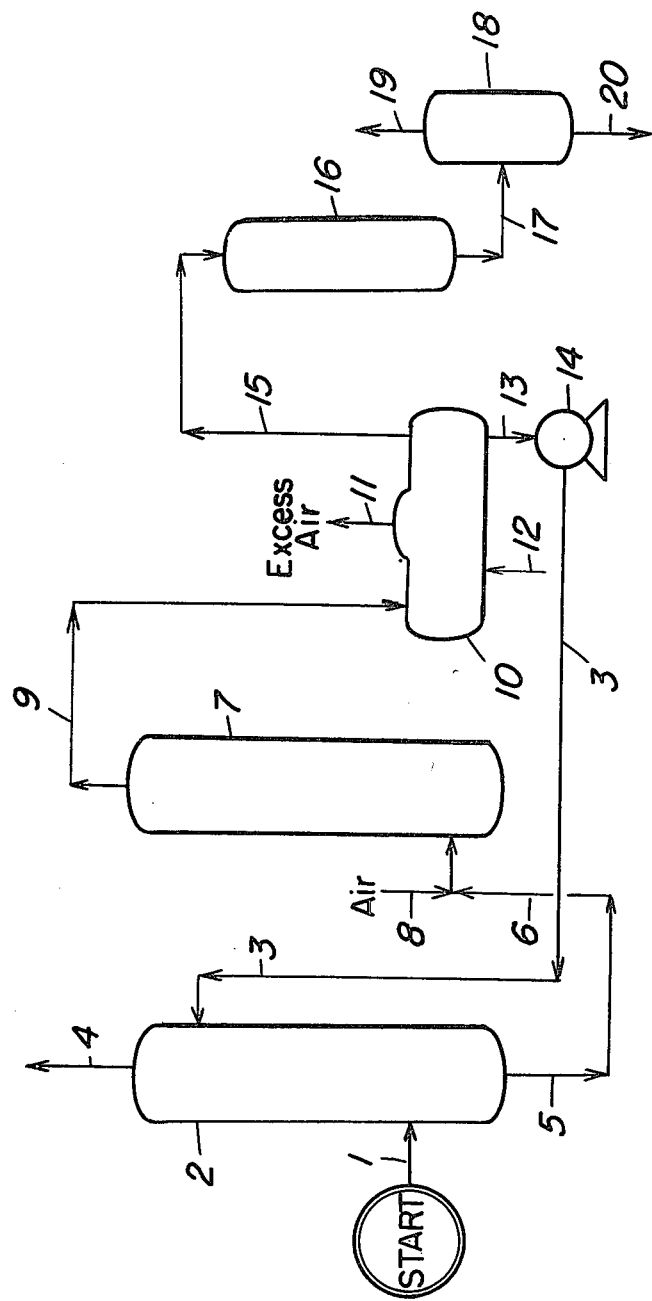

ZSM-5 ZEOLITE CATALYZES DIALKYL DISULFIDE CONVERSION TO HYDROGEN SULFIDE

BACKGROUND OF THE INVENTION

1. Field of the Invention

This invention is concerned with the conversion of dialkyl disulfides to hydrogen sulfide and useful hydrocarbons. More particularly, it is concerned with the disposal of dialkyl disulfide waste streams such as those produced in caustic extraction of mercaptans from gasoline or other liquid hydrocarbon products.

2. Prior Art

An unacceptable concentration of sulfur as aliphatic mercaptans is often encountered in the refining of liquid hydrocarbons to make gasoline, kerosine, jet fuel or heating oil, for example. These mercaptans, mostly in the $C_1$–$C_4$ range, are objectionable for a variety of reasons. In addition to imparting an unpleasant odor to the product, mercaptans attack copper alloys with the formation, in some instances, of gels or deposits; in all but the smallest quantity, mercaptans react with tetraethyl lead and reduce its anti-knock effectiveness. In all instances, sulfur compounds are converted to corrosive sulfur oxides on combustion, and emissions of these oxides deteriorate the quality of the air.

When the total sulfur content of the hydrocarbon product might be acceptable were it not for the mercaptan content, the refining industry sometimes resorts to non-extractive "sweetening" by oxidizing the mercaptans to dialkyl disulfides according to the general equation

$$R_1SH + R_2SH + \text{Oxidant} \rightarrow R_1SSR_2 \quad (1)$$

wherein $R_1$ and $R_2$ individually are alkyl groups that contain one or more carbon atoms. In such instances a variety of oxidants may be used including, by way of illustration, sodium plumbite and sulfur ("Doctor" process), or air in the presence of a catalyst (Merox sweetening). In all such instances the total sulfur content of the product is not substantially changed, the disulfides remaining in the product.

However, when the total sulfur content of a hydrocarbon stream is too high to produce an acceptable product, it becomes imperative to resort to removal of sulfur. Catalytic hydrotreating may be used for this purpose, and although highly effective it consumes costly hydrogen and converts the mercaptans to low molecular weight hydrocarbons of relatively low market value. In its favor, however, it is noted that catalytic hydrotreating converts the organic sulfur to hydrogen sulfide which is conveniently processed in a Claus unit to convert it to marketable sulfur. Thus, catalytic hydrotreating does not create a difficult waste disposal problem.

Another alternative available to the refiner is to extract aliphatic mercaptans with caustic soda. The mercaptans which are most objectionable, i.e. those in the $C_1$–$C_4$ range, fortuitously are the very ones which are most soluble in a caustic wash. A variety of caustic wash processes are available, most of them depending on the addition to the wash of one or more organic materials, sometimes referred to as "solutizers", which have been found to increase the solubility of the mercaptans. Such additives include cresoles and naphthenic acids, by way of illustration. The term "caustic wash", unless otherwise explicitly stated, will be used herein to refer broadly to any aqueous sodium hydroxide or potassium hydroxide solution of a concentration suitable for mercaptan extraction whether or not it contains, e.g., potassium cresylate. The various caustic wash processes are described in detail in a book by Dr. R. N. Maddox, "Gas and Liquid Sweetening", published by John N. Campbell, Norman, Okla. 73069, Library of Congress Catalog Card No. 73-91966. In particular, pages 202 to 220 of that volume are incorporated herein by reference for general background on the state of the art of liquid sweetening.

In the caustic wash process, the aqueous caustic solution, regardless of the presence or absence of "solutizers", becomes saturated with mercaptans. It may be regenerated by reboiling in the range of 220°–240° F. to strip the mercaptans. In a preferred operation, however, the mercaptans are oxidized, for example, by blowing with air in the absence or in the presence of a catalyst (e.g. Merox extraction). The disulfides formed on oxidation are usually insoluble in the caustic wash and may be decanted. The presence of potassium cresylate, however, tends to solubilize the disulfides. In such instances, the separation of the disulfides is facilitated, or may even require, extraction by a naphtha such as a straight-run naphtha boiling at 300°–400° F. Thus, for purposes of the present invention, caustic wash processes in which a naphtha extraction is used to assist in the separation of the aliphatic disulfides are contemplated along with other variants. For extraction by naphtha, one volume of the caustic wash may be contacted with about 0.1 to 5 volumes of the naphtha.

In general, a caustic wash process in which the caustic is regenerated by oxidation to the disulfides results in the production of a liquid waste stream consisting of one or more dialkyl disulfides that is difficult to dispose of. This waste stream is usually passed to a catalytic hydrodesulfurization unit where the disulfides are converted to hydrogen sulfide and alkanes having one to about four carbon atoms that are of relatively low market value. Although otherwise effective, the disposal of the waste stream places the process as a whole in a disadvantageous position compared with other alternatives because of the heavy burden placed on the catalytic hydrodesulfurization unit in handling a stream with a very high sulfur content.

It is an object of this invention to provide a novel method for disposing of a liquid stream consisting of a mixture of aliphatic dialkyl disulfides wherein each alkyl group has from one to about four carbon atoms. It is a further object of this invention to provide a method for converting such aliphatic dialkyl disulfides to hydrogen sulfide and hydrocarbon liquids. It is a further object of this invention to provide an improved caustic wash process for reducing the mercaptan content of a liquid hydrocarbon stream, the improvement consisting of an improved catalytic method for disposing of the disulfide waste stream. These and further objects will become apparent to one skilled in the art on reading this entire specification including the claims thereof.

A fairly large number of patents have appeared which are concerned with the conversion of aliphatic hetero atom containing compounds such as methanol and dimethyl ether to higher hydrocarbons. These patents generally utilize a crystalline zeolite such as ZSM-5 as catalyst. U.S. Pat. No. 3,894,107 issued July 8, 1975 to Butter et al. describes the conversion of aliphatic alcohols, aliphatic mercaptans, aliphatic sulfides and aliphatic halides to hydrocarbons. Example 25 thereof illustrates the conversion of methyl mercaptan. U.S. Pat. No. 3,894,106, issued on July 8, 1975 to Chang et al describes the conversion of aliphatic ethers, such as dimethyl ether, to aromatic hydrocarbons. U.S. Pat. No. 3,728,408 issued Apr. 17, 1973 to Tobias describes the conversion of polar organic compounds by catalytic contact with a crystalline aluminosilicate catalyst, the silica/alumina ratio of which is more than 10/1. Benzyl-disulfide is noted therein (Col. 7, line 1) along with numerous other sulfur-containing and sulfur-free compounds. ZSM-5 is included in the recitation of catalysts. The Examiner's attention is called also to a publication by C. D. Chang and A. J. Silvestri in the Journal of Catalysis, Vol. 47, pp. 247–259 (1977), particularly to Table 1 wherein the conversion of methyl mercaptan in the presence of ZSM-5 catalyst is reported.

The above references, although they do not suggest the present invention, are brought to the attention of the Examiner should he wish to consider them in his examination for patentability of the present invention. Applicants do not know of any other reference which, in their opinion, discloses or might be considered to suggest the present invention.

DESCRIPTION OF THE INVENTION

This invention provides a method for disposing of a liquid waste stream consisting of a mixture of aliphatic dialkyl disulfides $$R_3-S-S-R_4$$

wherein $R_3$ and $R_4$ individually are alkyl groups having one to about four carbon atoms. Disposal is effected by catalytically converting the stream to hydrogen sulfide and hydrocarbons as more fully described hereinbelow. This transformation is induced by contacting the stream at a temperature of 600° F. to 1000° F., preferably at about 700° F. to about 900° F., at a liquid hourly space velocity of about 0.2 LHSV to about 20 LHSV, preferably at about 0.5 LHSV to about 5 LHSV, at a pressure of about 15 psig to about 300 psig, with a crystalline zeolite catalyst characterized by a silica to alumina ratio of at least 12 and a Constraint Index of 1 to 12, as more fully described hereinbelow. It has now been found that such catalyst, even in the absence of added hydrogen, is remarkably effective in converting the described disulfides to hydrogen sulfide and a desirable mixture of hydrocarbons. More particularly, it has been found possible, even in a single pass, to so convert at least 90 wt.% of the disulfide feed, and even as much as 99 wt.% without recycle. Whereas the aliphatic dialkyl disulfide feed presents a troublesome disposal problem because of its very high sulfur content, the hydrogen sulfide conversion product is readily converted to salable sulfur by processes already in place in the modern refinery. The other conversion product, the mixture of hydrocarbons, consists predominantly of aliphatic hydrocarbons having at least three carbon atoms and a large fraction of aromatic hydrocarbons in the gasoline boiling range. Thus, this hydrocarbon stream may be fractionated and added to the high octane gasoline pool or otherwise treated to separate valuable fractions for petrochemicals. In contrast, when the waste disulfides stream is passed to the catalytic hydrodesulfurization unit, not only is hydrogen consumed but the hydrocarbon by-product consists only of hydrocarbons in the $C_1-C_4$ range.

In a preferred mode for operation by the method of this invention, conversion conditions are chosen within the above prescribed range to convert the disulfide stream to hydrogen sulfide and a hydrocarbon mixture that contains at least 20 wt.% aromatic hydrocarbons. It is preferred to conduct the conversion of the aliphatic disulfides in the absence of added hydrogen gas, although hydrogen may in some instances be used to extend the useful life of the catalyst.

It is a feature of this invention that if the aliphatic disulfide waste stream contains naphtha, it may still be processed as hereinabove described without prior concentration of the disulfides. Contemplated as within the scope of this invention is to process a mixture of aliphatic disulfides described above wherein the sulfur content of the mixture is from about 10 wt.% to about 60 wt.%.

The present invention also provides an improved process for reducing the sulfur content of a hydrocarbon stream contaminated by an aliphatic mercaptan such as methyl-, ethyl-, n-propyl-, isopropyl-, n-butyl-, sec-butyl-, tert-butyl-, isobutyl-mercaptan and mixtures thereof. This improved process will now be described in detail by reference to the drawing.

Applicant wishes at this point to indicate that the process which will now be described consists of a conventional caustic extraction process up to the point at which the waste stream is separated from the regenerated caustic wash. Since the conventional portion has a number of variants, all of which are known in the art, no great detail for this portion of the process will be given. One such variant which is commercially used is known as the Merox extraction process, and this is described in the September, 1978 issue at page 19 of Hydrocarbon Processing, published by Gulf Publishing Company, Houston, Tex. A more detailed description is found in Hydrocarbon Processing, Vol. 52, No. 2, Feb., 1973, pages 69–74. An important feature of the Merox process is that it utilizes a copper phthalocyanine oxidation catalyst in the caustic to facilitate conversion of the mercaptans to disulfides.

The feed to the process may be straight run gasoline, LPG, light naphtha, such as that boiling in the range of 150° to 250° F., and heavier stocks such as kerosine, heavy naphtha, jet fuel, etc. The process of this invention is particularly effective for materials in the gasoline boiling range. The feed is passed via line 1 to extraction tower 2 where it is contacted with caustic wash provided via line 3. The hydrocarbon feed of reduced sulfur content exits via line 4 and is passed to storage or other process facility as needed. The caustic wash which now contains dissolved mercaptans is passed from extraction tower 2 via lines 5 and 6 to regeneration vessel 7. Also passed to regeneration vessel 7 is air provided via line 8, which air reacts with the mercaptans to effect their conversion usually to a mixture of disulfide. The total effluent from regeneration vessel 7 passes via line 9 to separation vessel 10, from which excess air is withdrawn via line 11. In separation vessel 10, the mixture of aliphatic dialkyl disulfides, which is substantially insoluble in the caustic solution, separates from the regenerated caustic, forming two layers. The regenerated caustic is decanted from the vessel and passed via line 13 through pump 14 and from there via line 3 it is passed back to extraction tower 2, where it contacts fresh hydrocarbon feed. The disulfide waste layer is passed via line 15 to catalytic converter 16 where it is converted, as described above, to hydrogen sulfide and hydrocarbons. The conversion products are passed via line 17 to separation vessel 18 wherein the hydrogen sulfide and other light gases are flashed and withdrawn via line 19. The heavier hydrocarbons, which may include dissolved hydrogen sulfide, are withdrawn via line 20. The hydrogen sulfide withdrawn via line 19 is readily concentrated by known means, such as amine extraction, and may be readily converted to salable sulfur by passage to a Claus unit. The hydrocarbon stream withdrawn via line 20 may be processed by known methods to recover high octane gasoline, aromatic hydrocarbons, or other useful products.

In a variant of the above-described process, a naphtha wash may be introduced into separation vessel 10 via line 12 to facilitate the separation of the insoluble disulfides, which are soluble in naphtha, from the regenerated caustic. When this variant is used, generally about 0.1 to about 5 barrels of naphtha per barrel of caustic wash may be used. With this variant, the disulfide waste stream contains some naphtha diluent and the disulfide, dissolved in the naphtha, is withdrawn via line 15 and passed directly to catalytic reactor 16. In some instances, in addition to the conversion of the waste dialkyl disulfides, there may be measurable upgrading of the quality of the naphtha, which will of course be recovered via line 20.

In the foregoing description of the improved process of this invention, the improvement comprises the catalytic treatment of the waste disulfides stream withdrawn via line 15 whether or not it contains naphtha diluent. In general, the total waste stream withdrawn via line 15 will have a sulfur content of about 10 to about 60 wt.%.

The catalyst and catalytic reaction conditions employed in vessel 16 are those hereinabove described.

The method and process of this invention depends on the utilization of a particular crystalline zeolite catalyst which will now be described in detail.

The crystalline aluminosilicates utilized herein are members of a novel class of zeolites that exhibit unusual properties. Although these zeolites have unusually low alumina contents, i.e. high silica to alumina ratios, they are very active even when the silica to alumina ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning with oxygen-containing gas such as air.

An important characteristic of the crystal structure of this class of zeolites is that it provides constrained access to and egress from the intracrystalline free space by virtue of having an effective pore size intermediate between the small pore Linde A and the large pore Linde X, i.e. the pore windows of the structure have about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The zeolites useful in this invention have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although in some instances excessive puckering of the rings or pore blockage may render these zeolites ineffective. 12-membered rings usually do not offer sufficient constraint to produce the advantageous conversion, although the puckered 12-ring structure of TMA offretite shows constrained access. Other 12-ring structures may exist which, due to pore blockage or to other cause, may be operative.

Rather than attempt to judge from crystal structure whether or not a zeolite possesses the necessary constrained access to molecules larger than normal paraffins, a simple determination of the "Constraint Index" as herein defined may be made by passing continuously a mixture of an equal weight of normal hexane and 3-methylpentane over a small sample, approximately one gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature is adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is calculated as follows:

Constraint Index =

$$\frac{\log_{10} \text{(fraction of n-hexane remaining)}}{\log_{10} \text{(fraction of 3-methylpentane remaining)}}$$

The Constraint Index approximates the ratio of the cracking rate constants for the two hydrocarbons. Zeolites suitable for the present invention are those having a Constraint Index of 1 to 12. Constraint Index (CI) values for some typical zeolites are:

| CAS | C.I. |
| --- | --- |
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| TMA Offretite | 3.7 |
| Beta | 0.6 |
| H-Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby have different Constraint Indexes. Constraint Index seems to vary somewhat with severity of operation (conversion) and the presence or absence of binders. Therefore, it will be appreciated that it may be possible to so select test conditions to establish more than one value in the range of 1 to 12 for the Constraint Index of a particular zeolite. Such a zeolite exhibits the constrained access as herein defined and is to be regarded as having a Constraint Index of 1 to 12. Also contemplated herein as having a Constraint Index of 1 to 12 therefore within the scope of the novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value of 1 to 12. Thus, it should be understood that the Constraint Index value as used herein is an inclusive rather than an exclusive value. That is, a zeolite when tested by any combination of conditions within the testing definition set forth hereinabove and found to have a Constraint Index of 1 to 12 is intended to be included in the instant catalyst definition regardless that the same identical zeolite tested under other defined conditions may give a Constraint Index value outside of 1 to 12.

The class of zeolites defined herein is exemplified by ZSM-5, ZSM-11, ZSM-12, ZSM-23, ZSM-35, ZSM-38, and other similar materials. U.S. Pat. No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particularly described in U.S. Pat. No. 3,832,449, the entire content of which is incorporated herein by reference.

ZSM-23 is more particularly described in U.S. Pat. No. 4,076,842, the entire content of which is incorporated herein by reference.

ZSM-35 is more particularly described in U.S. Pat. No. 4,016,245, tne entire content of which is incorporated herein by reference.

ZSM-38 is more particularly described in U.S. Pat. No. 4,046,859, the entire content of which is incorporated herein by reference.

The specific zeolites described, when prepared in the presence of organic cations, are substantially catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminsolicates are ZSM-5, ZSM-11, ZSM-12, ZSM-23, ZSM-35, and ZSM-38, with ZSM-5 being particularly preferred.

In a preferred aspect of this invention, the zeolites hereof are selected as those having a crystal framework density, in the dry hydrogen form, of not less than about 1.6 grams per cubic centimeter. It has been found that zeolites which satisfy all three of these criteria are most desired for several reasons. When hydrocarbon products or by-products are catalytically formed, for example, such zeolites tend to maximize the production of gasoline boiling range hydrocarbon products. Therefore, the preferred zeolites of this invention are those having a Constraint Index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space. It is possible that the unusual sustained activity and stability of this class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites including some which are not within the purview of this invention are:

| Zeolite | Void Volume | Framework Density |
|---|---|---|
| Ferrierite | 0.28 cc/cc | 1.76 g/cc |
| Mordenite | .28 | 1.7 |
| ZSM-5,-11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing the desired conversion process, it may be desirable to incorporate the above-described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix on an anhydrous basis may vary widely with the zeolite content ranging from between about 1 to about 99 percent by weight and more usually in the range of about 5 to about 80 percent by weight of the dry composite.

The method and process of this invention will now be illustrated by example. All parts and proportions are by weight unless otherwise explicitly specified. The examples are for the purposes of illustrating the invention and are not to be considered as limiting thereon, the scope of the invention being determined by the entire specification and claims appended thereto.

EXAMPLE 1

Di-tert-butyl disulfide was passed over 6 cubic centimeters of HZSM-5 catalyst contained in a catalytic reactor. The temperature in the reactor was maintained at about 800° F. (430° C.). The feed was passed at a rate of 1 liquid hourly space velocity. The product was separated into a gaseous fraction and a liquid fraction. Analysis of the products showed substantial complete conversion (more than 99.5 wt.%) of the feed. The gaseous products and the liquid products were analyzed for hydrogen sulfide content, and it was found that 99 wt.% of the sulfur in the feed had been converted to hydrogen sulfide. In addition, a small amount of carbonyl sulfide was found in the gas, together with a trace of dimethyl sulfide. The material balance for sulfur calculated to 100.2% of the sulfur in the feed which, within experimental error, indicates substantially complete conversion. The hydrocarbon distribution found for the products was as follows:

| HYDROCARBON DISTRIBUTION, WT. % | |
|---|---|
| Methane | .33 |
| Ethane | .88 |
| Ethylene | 1.37 |
| Propane | 18.74 |
| Propylene | 2.10 |
| Isobutane | 16.85 |
| n-Butane | 5.83 |
| Butenes | .76 |
| $C_5{}^+$ PON | 5.20 |
| AROMATICS | |
| $A_6$ | 2.82 |
| $A_7$ | 14.97 |
| $A_8$ | 18.77 |
| $A_9$ | 6.10 |
| $A_{10}$ | 1.99 |
| $A_{11}{}^+$ | 3.29 |
| Total | 47.94 |

EXAMPLE 2

The feed and procedure employed in Example 1 was repeated utilizing the same charge of catalyst, except that the liquid hourly space velocity was reduced from 1.0 to 0.66. The duration of the run was four hours, and again substantially complete conversion of the feed was observed. The distribution of hydrocarbon products found in this example was as follows:

| HYDROCARBON DISTRIBUTION, WT. % | |
|---|---|
| Methane | .07 |
| Ethane | .91 |
| Ethylene | 1.14 |

| -continued | |
|---|---|
| Propane | 17.29 |
| Propylene | 1.78 |
| Isobutane | 17.39 |
| n-Butane | 5.38 |
| Butenes | .65 |
| $C_5^+$ PON | 4.71 |
| AROMATICS | |
| $A_6$ | 3.22 |
| $A_7$ | 16.10 |
| $A_8$ | 18.30 |
| $A_9$ | 6.41 |
| $A_{10}$ | 2.40 |
| $A_{11}^+$ | 4.25 |
| Total | 50.68 |

What is claimed is:

1. A method for disposing of a liquid stream consisting of a mixture of dialkyl disulfides wherein the alkyl groups individually have from one to about four carbon atoms, which method comprises contacting said stream under a combination of conditions that include a temperature of about 600° F. (305° C.) to about 1000° F. (538° C.), a liquid hourly space velocity of about 0.2 LHSV to about 20 LHSV, and a pressure of about 15 psig to 300 psig, with a crystalline zeolite catalyst having a silica to alumina ratio of at least 12 and a Constraint Index of 1 to 12, said combination of conditions being effective to convert said dialkyl disulfides to hydrogen sulfide and a mixture of hydrocarbons.

2. The method described in claim 1 wherein said liquid stream has a sulfur content of about 10 to about 60 wt.%.

3. The method described in claim 1 wherein said contacting conditions include a temperature of about 700° F. (371° C.) to about 900° F. (482° C.), and said liquid hourly space velocity is about 0.5 LHSV to about 5 LHSV.

4. The method described in claim 3 wherein said liquid stream has a sulfur content of about 10 to about 60 wt.%.

5. The method described in claim 1 wherein said crystalline zeolite is HZSM-5.

6. The method described in claim 2 wherein said crystalline zeolite is HZSM-5.

7. The method described in claim 3 wherein said crystalline zeolite is HZSM-5.

8. The method described in claim 4 wherein said crystalline zeolite is HZSM-5.

9. The method described in claim 1 or claim 2 or claim 3 or claim 4 or claim 5 or claim 6 or claim 7 or claim 8 wherein at least 90 wt.% of said dialkyl disulfides are converted to hydrogen sulfide and hydrocarbons.

10. In a process for reducing the sulfur content of a hydrocarbon contaminated by one or more aliphatic mercaptans wherein the alkyl group has from one to about four carbon atoms, said process comprising treating said hydrocarbon with an aqueous caustic wash thereby dissolving said mercaptans in said caustic wash, separating said mercaptan-containing caustic wash from said hydrocarbon, oxidizing said mercaptans in said wash thereby forming aliphatic disulfides waste insoluble in said caustic wash and regenerating said caustic wash, separating wash and disposing of said waste, the improvement which comprises:

disposing of said aliphatic disulfides waste by contacting the same with a crystalline zeolite catalyst having a silica to alumina ratio of at least 12 and a Constraint Index of 1 to 12, said contacting being effected at a temperature of about 600° F. (305° C.) to about 1000° F. (538° C.) and a liquid hourly space velocity of about 0.2 LHSV to about 20 LHSV thereby converting said disulfide waste to hydrogen sulfide and a mixture of hydrocarbons, and converting said hydrogen sulfide to sulfur.

11. The method described in claim 10 wherein said crystalline zeolite catalyst is HZSM-5.

* * * * *

UNITED STATES PATENT AND TRADEMARK OFFICE
CERTIFICATE OF CORRECTION

PATENT NO. : 4,265,735
DATED : May 5, 1981
INVENTOR(S) : C.A. Audeh, C.D. Chang and W.H. Lang It is certified that error appears in the above-identified patent and that said Letters Patent are hereby corrected as shown below:

| | |
|---|---|
| Col. 7, line 42 | "1 to 12 therefore" should be --1 to 12 and therefore-- |
| Col. 8, line 5 | ", tne entire content" should be --, the entire content-- |
| Col. 10, line 17 | "Di-tert-butyl" should be --Di-_tert_-butyl-- |
| Col. 12, line 27 | Should read --wash, separating said aliphatic disulfides waste from said regenerated wash and disposing of said waste, . . .-- |

Signed and Sealed this

Eleventh Day of August 1981

[SEAL]

Attest:

Attesting Officer

GERALD J. MOSSINGHOFF

Commissioner of Patents and Trademarks